United States Patent [19]
Kleinert et al.

[11] Patent Number: 5,511,425
[45] Date of Patent: Apr. 30, 1996

[54] FLAW DETECTOR INCORPORATING DGS

[75] Inventors: Wolf-Dietrich Kleinert, Bonn, Germany; John M. Cuffe, Centre County, Pa.; Theodore L. Ballenger, Mifflin County, Pa.; Alan D. Weiner, Perry County, Pa.; Mark H. Feydo, Mifflin County, Pa.

[73] Assignee: Krautkramer-Branson, Inc., Lewistown, Pa.

[21] Appl. No.: 164,210

[22] Filed: Dec. 9, 1993

[51] Int. Cl.⁶ .................................................. G01N 29/04
[52] U.S. Cl. ................................................ 73/627; 73/609
[58] Field of Search ........................... 73/598, 600, 627, 73/602, 631, 609

[56] References Cited

U.S. PATENT DOCUMENTS

| | | | |
|---|---|---|---|
| 4,102,205 | 7/1978 | Pies et al. | 73/626 |
| 4,147,065 | 4/1979 | Lather et al. | 73/611 |
| 4,207,593 | 6/1980 | Deutsch et al. | 358/106 |
| 4,271,705 | 6/1981 | Crostack | 73/602 |
| 4,513,621 | 4/1985 | Rengel et al. | 73/631 |
| 4,523,468 | 6/1985 | Derkacs et al. | 73/598 |
| 4,658,648 | 4/1987 | Roddeck et al. | 73/597 |
| 4,669,312 | 6/1987 | Maurer | 73/600 |
| 4,695,797 | 9/1987 | Deutsch et al. | 324/230 |
| 5,138,269 | 8/1992 | Deutsch | 324/715 |

*Primary Examiner*—Richard Chilcot
*Assistant Examiner*—Max H. Noori
*Attorney, Agent, or Firm*—Polster, Lieder, Woodruff & Lucchesi

[57] ABSTRACT

Apparatus (10) for performing ultrasonic flaw testing of a material (M) or assembly. A pulser (28) generates an electrical pulse having defined characteristics. A transducer (12) converts the signal to an ultrasonic pulse, propagates the pulse through the material or assembly, receives an echo the characteristics of which include reflections off flaws or discontinuities in the material or assembly, and converts the echo into an electrical reply signal. The transducer is selectable from among a number of transducers. A processor (32) processes the reply signal to produce a visual display representing the amplitude of the reply signal for a range of propagation times (distances) into the material. A visual display (16) displays the processed electrical signal. A correlation module (42) generates a gate signal which is visually displayed (at 38) with the processed electrical signal. The gate signal corresponds to a maximum amplitude value which represents the maximum flaw size allowable for the test. If the displayed amplitude of the processed electrical signal exceeds the maximum amplitude value, the material or assembly fails the test. The correlation module emulates a series of DGS curves for the transducer used during the test. This is done to take into account test parameters related to the transducer and the material, so after an initial calibration of the apparatus is performed using a selected transducer and a reference reflector, valid test results are obtained with the transducer regardless of the distance of the reflector.

11 Claims, 3 Drawing Sheets

D G S CURVE FOR A SMALL REFLECTOR

FLAW DETECTOR INCORPORATING DGS

BACKGROUND OF THE INVENTION

This invention relates to ultrasonic flaw detectors for detecting flaws in material, structural assemblies, etc., and, more particularly, to an ultrasonic flaw detector implementing DGS curves and a method for implementing and using curves in such a detector.

Ultrasonic flaw detection is used in many manufacturing applications to detect imperfections within structural elements. As is well-known in the art, the detection method involves generation a sound wave or pulse, transmitting the pulse through a transducer or probe into the material, listening for a sound return, an echo or "ping", and then evaluating the characteristics of the echo. The amplitude of the echo is a function of a number of factors; these include, the frequency of the sound wave, the sound transmission characteristics of the material being tested, the size of the flaw, and the transit time of the pulse from its point of injection into the material to the discontinuity and the return time. Recently, flaw detector instrumentation has been developed which not only electronically processes the returns from a flaw detection test, but also provides both digital results of the test together with a graphic display of a return. This allows a user to readily view an amplitude versus distance display of the test result. For determining whether or not the material under test passes a particular test, the display may include some type of reference indication which visually represents the maximum allowable echo amplitude which is acceptable. If the displayed amplitude exceeds this "go/no-go" indication, the material or assembly fails the test. The acceptance level is also based upon a number of factors related to the material or structure, etc.

It will be appreciated that with a point source of sound transmission such as is provided by a transducer, the transmitted pulse will disperse in a geometric manner. This, together with the normal attenuation resulting from passage of the pulse through the material requires that the amplitude of the processed echo be corrected based on these considerations. Otherwise, for example, the displayed amplitude of the processed echo may be such that a part which is actually faulty could be accepted, because the flaw may be sufficiently deep into the material that the processed, attenuated amplitude of the echo for that depth falls within the acceptable range of values.

This problem has been recognized and various approaches have been taken to attempt to adjust the measured values for these factors so the adjusted result is an accurate indication of the test result. One approach which has been used involves distance gain sizing (DGS) and uses a DGS curve. DGS is also referred to as AVG in Europe. In use, a DGS curve is actually a series of curves, separate ones of which are created for not only each of the types of probes or transducers which are used, but also for the range or depth of material which is being tested, the overall system gain of the testing device, and similar related parameters. There may be 10–15 curves for each type of transducer used. The curves provide a compensation factor to adjust the measured amplitude of an echo so the corrected amplitude can be compared against the reference to determine whether a test is passed or failed. DGS curves have been in use for some time. However, while they provide a high degree of correctabilty, the need for a wide variety of charts, and the limitations the charts impose, has made this approach cumbersome to use. For example, if a baseline is made for calibration purposes using a particular transducer and range of reflections, all subsequent tests had to be made within the same ranges or else a new baseline established each time the range is changed. The recently developed electronic instrumentation does not use DGS because of the various drawbacks outlined above.

DGS is a methodology which was developed in Germany in 1958. During this period, a separate compensation methodology known as distance-amplitude correction, or DAC, was developed in the United States. This DAC procedure involves measuring the response from a known reflector (a 0.064-inch diameter disk, for example) at different distances from a source. The responses are then used to develop correction factors so that the amplitude of the response is constant for the range of measured distances. It will be understood that either approach is a valid way by which test data can be interpreted to determine the acceptability of material under test.

Although electronic based flaw detectors are currently in use which employ DAC as part of the processing methodology, there is still a desire to use DGS curves with such instruments. For the digital instrumentation now available, people have prepared transparent overlays of the curves which fit over the display screen. Others use a grease pencil or similar implement to draw an appropriate DGS curve on the faceplate over the display. Not only are these approaches impractical, the user still must have available a large number of DGS curves for use under a wide range of test conditions. Or else, the instrument can only be configured for use with one type transducer, for example, and during the testing there can be no change in the transducer, the instrument's gain setting, testing range, offset or delay, etc.

SUMMARY OF THE INVENTION

Among the several objects of the present invention may be noted the provision of an ultrasonic flaw detector for testing materials and structures, the provision of such a flaw detector which incorporates a DGS data processing strategy and method; the provision of such a flaw detector in which the DGS automatically compensates processed echo responses; the provision of such a DGS compensation method which allows the flaw detector to provide a visual display of flaw test results in which factors such as system gain, range, and delay are automatically taken into account; the provision of such a method by which the user can readily and accurately determine whether or not a material passes a test; the provision of such a flaw detector to electronically incorporate DGS curves for various transducers which graphically represent systems gain levels required to bring the amplitude of an echo or response to a known reflector to a predetermined level as a function of distance in length near field; the provision of such a flaw detector to electronically incorporate an entire series of DGS curves for different types of transducers and different types of reflectors; the provision of such detector which enables the user to set an initial calibration using one type of transducer and reflector, and then subsequently tests with a different reflector, the results of the tests being accurately displayed for the user without the user having to recalibrate the instrument or refer to DGS curves or display overlays to evaluate the test results; the provision of such a test method which gives the user greater flexibility in performing ultrasonic testing; the provision of such an ultrasonic flaw detector which is easy to use and can be used for a wide variety of tests; and, the provision of such a detector and method which allow tests to be performed in Germany and other European countries where materials must comply with design specifications requiring testing based upon DGS standards.

In accordance with the invention, generally stated, apparatus is disclosed for performing ultrasonic flaw testing of a material or assembly. A pulser generates an electrical pulse having defined characteristics. A transducer converts the signal to an ultrasonic pulse, propagates the pulse through the material or assembly, receives an echo the characteristics of which include reflections off flaws or discontinuities in the material or assembly, and converts the echo into an electrical reply signal. The transducer is selectable from among a number of transducers. A processor processes the reply signal to produce a visual display representing the amplitude of the reply signal for a range of propagation times (distances) into the material. A visual display displays the processed electrical signal. A correlation module generates a gate signal which is visually displayed with the processed electrical signal. The gate signal corresponds to a maximum amplitude value which represents the maximum flaw size allowable for the test. If the displayed amplitude of the processed electrical signal exceeds the maximum amplitude value, the material or assembly fails the test. The correlation module emulates a series of DGS curves for the transducer used during the test. This is done to take into account test parameters related to the transducer and the material, so after an initial calibration of the apparatus is performed using a selected selected transducer and a reference reflector, valid test results are obtained with the transducer regardless of the size of the reflector. A method of performing ultrasonic flaw testing is also disclosed. Other objects and features will be in part apparent and in part pointed out hereinafter.

BRIEF DESCRIPTION OF THE DRAWINGS

Corresponding reference characters indicate corresponding partsthroughout the drawings.

DESCRIPTION OF A PREFERRED EMBODIMENT

Figure 2:
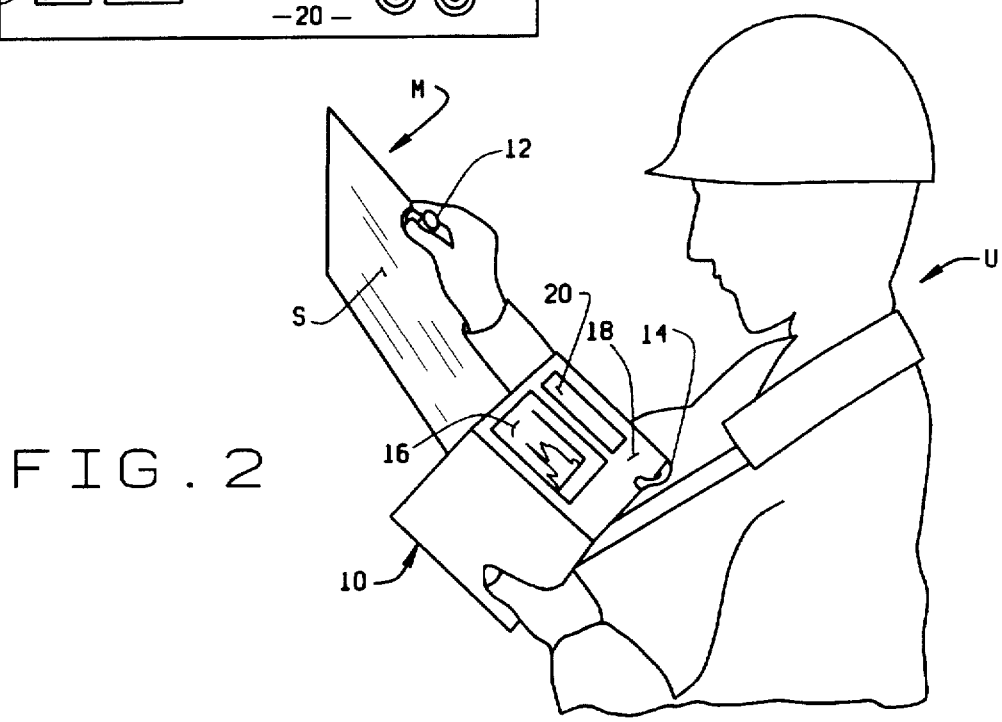
FIG. 2 is illustrates usage of flaw detector instrument in performing a test.
Figure 7:
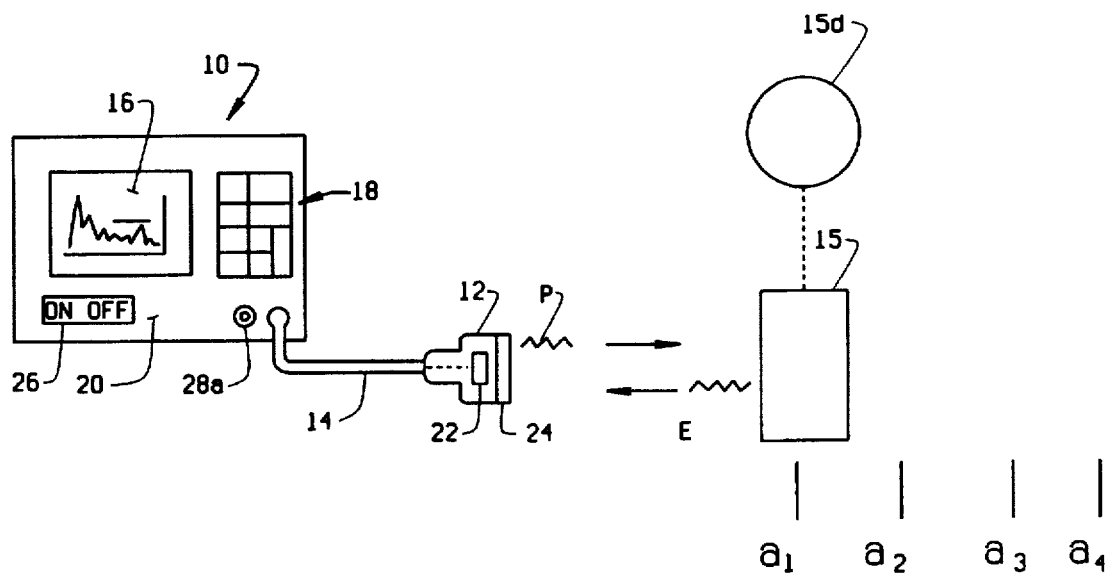

Referring to the drawings, an ultrasonic flaw detection test is shown in FIG. 2 as being performed on a piece of material M. The material could be tested prior to installation into an assembly, or thereafter. In FIG. 2, a technician or user U is shown holding a portable ultrasonic flaw tester 10. The instrument may be a hand held portable instrument, as shown, or it could a rack mounted type instrument. Regardless, the user first connects a probe or transducer 12 to the instrument via a test cable 14; and, then using a known reference reflector 15 (see FIG. 7), calibrates the instrument. Calibration of the instrument involves generating and transmitting an ultrasonic pulse P having known pulse characteristics at the reference reflector 15. The reference reflector may be disk shaped reflector such as reflector 15d (bottom hole drilled from the back of material M) having a known diameter and positioned a known distance from the transducer. For each distance from the source or probe to the reflector, a known ultrasonic pulse will produce an echo E having known characteristics. By viewing the response echo characteristics on the apparatus display 16, the user can adjust the display, using controls 18 on a front panel 20 of the apparatus, until the reference echo is displayed on the screen with a measurable amplitude. The user may then use this echo as his calibrated reference. In FIG. 7, reflector 15 is shown to be a backwall or plate reflector. Other types of standard calibration reflectors can be used for calibration purposes such as the disc reflector 15d referred to above. It will be understood that there are a number of probes which are used in flaw detector testing and that there are a variety of transducer/reflector combinations which may be used depending on the tests being performed.

After calibration, the user positions the transducer adjacent a surface S of the material and causes an ultrasonic signal or pulse to be transmitted through the material. The pulse, for example, has a frequency of 5 MHz. Transducer 12 includes a crystal 22 for converting an input electrical signal generated by instrument 10 into the ultrasonic signal propagated into surface S of the material. The probe has a cover plate or shield 24 which is positioned adjacent surface S and through which the ultrasonic pulse is propagated into the material.

As is well-known in the art, pulse transmission through the material is effected by discontinuities (flaws) which are present in the material. The purpose of the test is to determine if the material or assembly is acceptable, or if any of these flaws are so significant that the material or assembly must be rejected. The response or echo produced by transmission of the pulse propagates back through the material to transducer 12. When it is received back at the transducer, crystal 22 reconverts the sound wave back into an electrical signal which is processed to provide a visual display on the display screen 16 of the detector.

Figure 1:
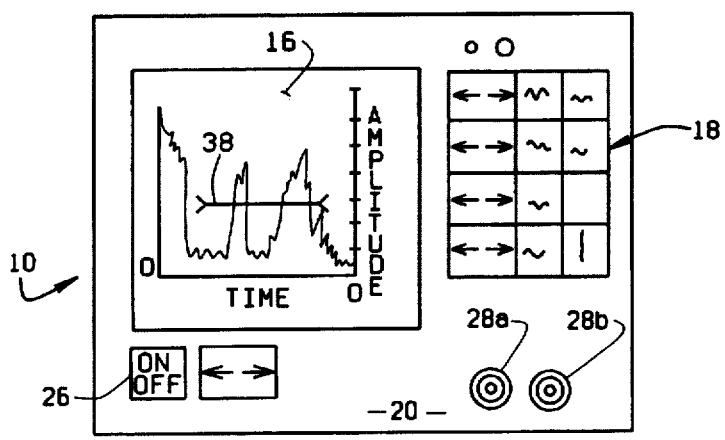
FIG. 1 is a representation of the front panel of an ultrasonic flaw detector showing various controls and a display.
Figure 3:
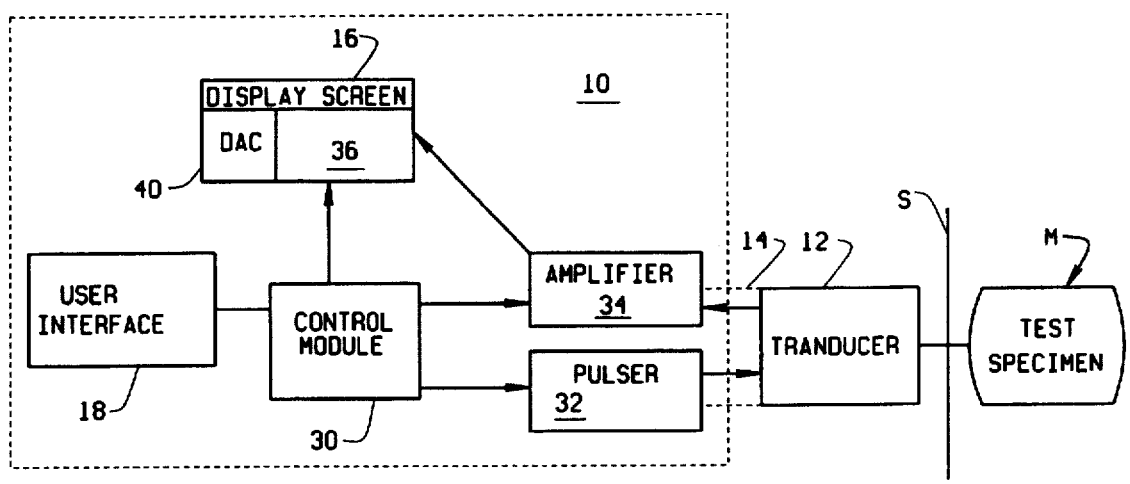
FIG. 3 is a block diagram of a prior art ultrasonic flaw detector.

FIG. 1 illustrates the front panel 20 of instrument 10. Display screen 16 forms a portion of the panel. The control portion 18 of front panel 20 includes a keypad section which comprises a user interface for the instrument. An ON/OFF switch 26 located on the front panel is for powering the instrument, and connectors 28a, 28b for connecting different types of transducers to the instrument. As shown in FIG. 3, Once transducer 12 is positioned adjacent the surface S of the material, a control module 30 of the instrument provides an input to a pulser module 32. The pulser module generates an electrical pulse whose signal characteristics (frequency, amplitude, pulse width, rise time, fall time, etc.) are a function of the control inputs from module 30. The pulse output is supplied to transducer 12 which converts the electrical energy to a sonic energy burst. The reflected energy or echo is converted by the transducer back into electrical energy. This return is amplified by an amplifier 32 and supplied to a signal processor module 36. The user, through interface module 18, has supplied information to the instrument as to the type of transducer being used for a particular test. The control module supplies this and other relevant information to the processor module. The processor using this information and the amplified return signal, produces a time-amplitude display on screen 16 such as shown in FIG. 1.

In FIG. 1, the real time display of the echo can be evaluated by the user. The general theory of flaw detection is that a bigger reflector returns more sound energy. Hence, the bigger the amplitude of the echo, the bigger the flaw. In determining whether or not the material passes a test, the user evaluates the display to see if the flaw echo is greater than a certain percentage of the screen height. For help in this evaluation, the processor generates a reference bar or line 38 on the display screen. This line is commonly referred to as a gate. If the echo amplitude stays below the level of the gate, the material passes. If not, it fails.

Figure 4:
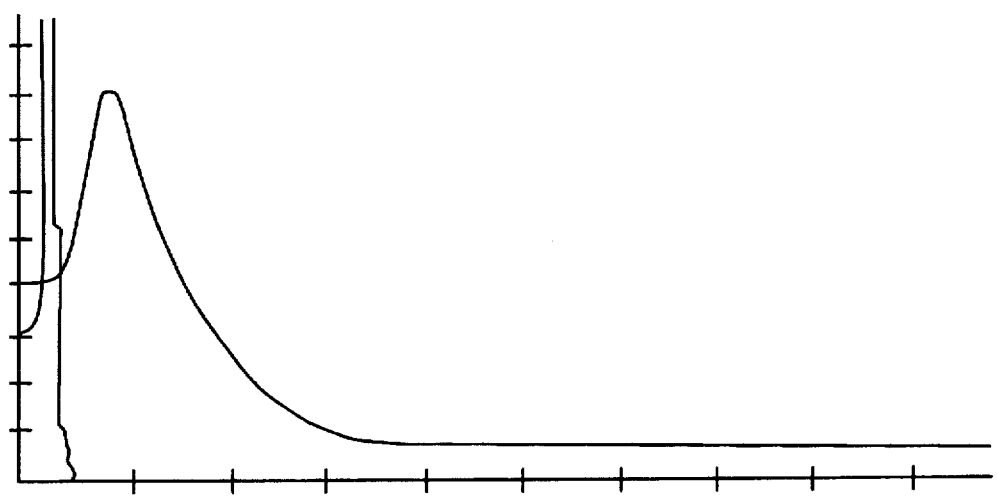
FIG. 4 is a graph showing the profile of the reflected sound field intensity emanating from a transducer for a small reflector.

Referring to FIG. 4, there is shown a response profile for a sound transducer 12 of the type used for ultrasonic flaw testing. The profile or response curve shown represents the reflected sound field intensity emanating from the transducer as it is effected by the characteristics of a material. These characteristics include the propagation rate or velocity of the pulse through the material, and the sound attenuation of the material. The profile further shows the efffects of geometry which must be considered. That is, the profile reflects movement of a constant reflector away from the transducer. As discussed in the Background section of this application, it is important for evaluation purposes that the flaw detection be relative to the size of the reflector at any distance away from the transducer. As noted above, the bigger the flaw the greater should be the amplitude of the echo. The distance, for purposes of a flaw detector, is the near field distance. Heretofore, to provide a correct visual display 16, processor 36 of instrument 10 has included the distance-amplitude compensation strategy DAC also previously referred to. As described, DAC involves measuring the response from a known reflector at various distances from a transducer. The resulting correction factors are incorporated in processor 30 so the displayed amplitude on display 16 is constant for the range of distances in the material through which the sound propagated. In effect, the processor includes a schedule 40 which contains compensation factors. When the user sets-up instrument 10 for use during calibration, he indicates the type of transducer he will be using, system gain, etc. By entering this information through interface 18, or selecting these operating parameters, he informs the processor, through control module 30, as to which portion of the schedule is to be used for the tests being performed.

There is a separate amplitude compensation strategy for producing a gate 38 by which the displayed amplitude response of an echo E is evaluated to determine acceptability of the material. This alternate strategy is a distance-gain strategy or DGS. DGS has heretofore required the preparation and use of a series of graphs such as the graph shown in FIG. 5. The DGS strategy allows calculation of an echo response for an equivalent reflector size based on certain parameters relating to the probe or transducer characteristics, the material under test, and operating characteristics of amplifier 34 and processor 36 of the flaw detector apparatus. An advantage of the DGS strategy is that once a transducer 12 and reflector 15 have been calibrated together, compensation can be made for the transducer regardless of size reflector subsequently used.

Figure 5:
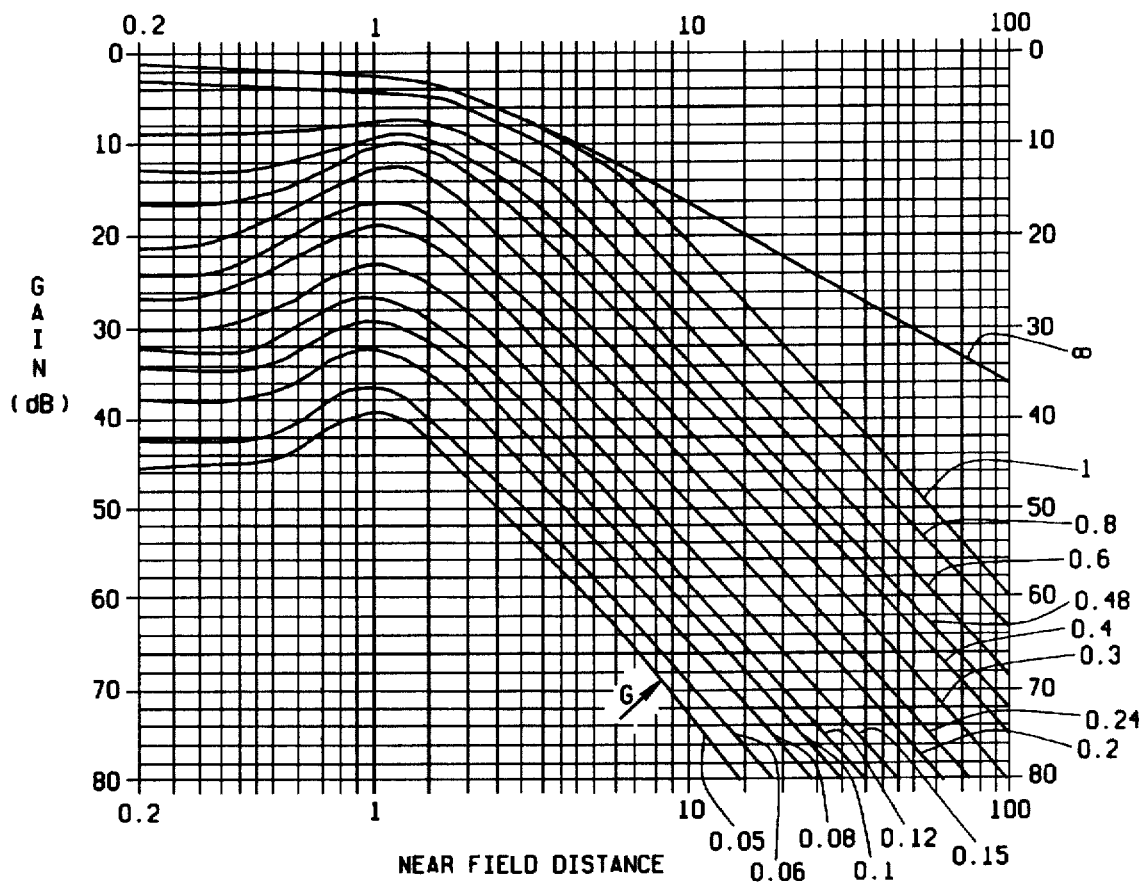
FIG. 5 is a representative DGS curve for a particular transducer and measures required gain as function of near field distance.

As seen in FIG. 5 there are a series of curves which are plotted on the graph. The abscissa of the graph represents dB of gain required to bring the peak amplitude of an echo to a known percentage of vertical elevation on the scale of display 16. The ordinate of the graph is near field length between a known transducer and reflector. Near field length is a function of sound velocity. This value can be calculated as follows:

$$N = \frac{(Drms)^2 f}{4c}$$

where Drms=0.95 Do. For the above equation,
Do is the real diameter of transducer 12,
Drms is the effective transducer diameter,
f is the operating frequency of the transducer, and
c is the sound velocity.

The series of curves plotted on the graph of FIG. 5 are a function of the size of a reflector and transducer parameters. It will be understood that there is a generic curve for each transducer and reflector, this curve representing a normalized set of data. The curves shown in the graph of FIG. 5 are derived from this normalized curve. A portion of this derivation is empirical. In particular, the starting point on the abscissa for each curve is empirically determined. As discussed in the Background section of this application, while the DGS compensation strategy is not new, it is not easy to use because of the number of curves involved. As noted, use of this approach with an instrument such as apparatus 10 has heretofore involved the use of transparencies on which curves are drawn, there being a series of transparencies or overlays for the different probes with which tests are performed. transparent screen (not shown) which overlays display 16 is written on with a grease pencil, for example. In either event, the transparencies or markings are used to draw the sound response (in time) of a known reflector for a transducer at a constant instrument setting. The setting was established during the calibration. If, during the test, a different transducer is employed, the instrument is set to a different range so the user can investigate a detected flaw, or other instrument settings (gain, for example) are changed, the user must employ a different overlay or clean the screen and draw a new set of curves.

The DGS curves of FIG. 5 represent gain differencies obtained with reflectors, for example disc reflectors, of varying equivalent reflector size (ERS) as a function of the distance between a transducer 12 and the reflector. The relationship is effected both by the type of transducer used and the material. However, it will be understood that the gain values shown are only relative values. A reference point must be determined for each test as a funtion of the probe used in a particular test. The uniform gain curves G plotted in FIG. 5 can be described by the following relationship:

G=G(x,y), where x=a/N, and y=ERS/d. As used in this equation,
G is relative gain in dB,
a is the distance between the transducer and
reflector,
N is the near field length,
ERS is, as noted, the equivalent reflector size, and
D is the diameter of the transducer.

From this general equation, a general DGS diagram can be transformed into a specialized diagram which takes into account the gain Gs for a given material with a sound velocity Ct, and a transducer 12 which is characterized by its operating frequency f, a delay line length Id which represents an imaginary length corresponding to the propagation time of ultrasonic sound at the transducer frequency through the transducer, and the sound velocity Cd through the delay line.

Figure 6:
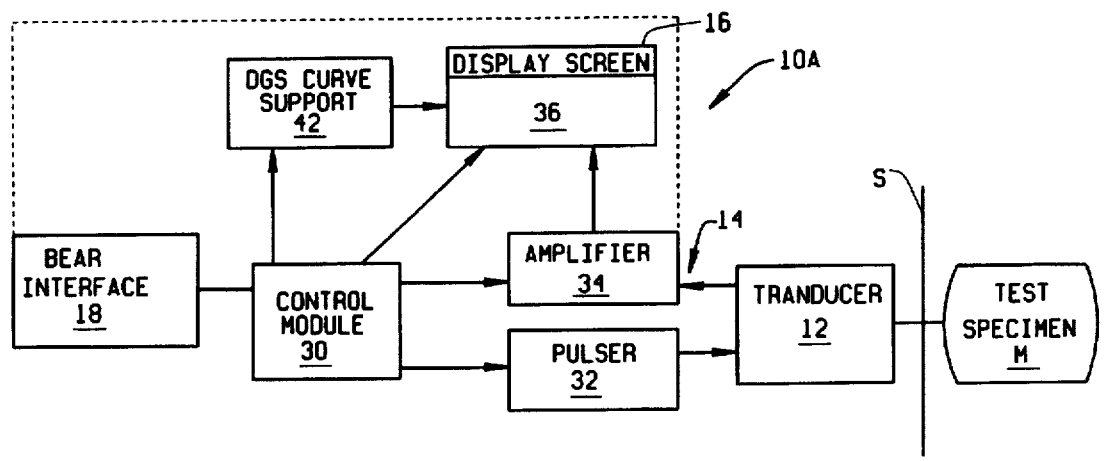
FIG. 6 is a block diagram of an improved flaw detector of the present invention incorporating DGS; and, FIG. 7 illustrates calibration of the apparatus using a probe selected for the test to be performed, and a known reflector.

Referring to FIG. 6, ultrasonic flaw testing apparatus 10A of the invention includes the control module 30 with its associated user interface 18. Pulser module 32 generates the electrical output pulse supplied to transducer 12. Again, the return echo is converted by the transducer back into an electrical signal which is amplified by amplifier 32 and supplied to signal processor 36. As previously described, processor 36 uses inputs from control module 30 to process the amplified return signal and produce the time-amplitude display on screen 16. Apparatus 10A includes a correlation means or module 42 by which the DGS strategy is implemented into the signal processing. Thus, display 16 will be compensated using the stored analog of an appropriate DGS curve, the information from which the curve would be constructed being stored in module 42.

The information stored in module 42 includes the following:

a) model or other identification of each probe used in testing for presetting probe parameters, b) diameter of the crystal used in the probe, c) the crystal's operating frequency, d) type of reflector used for calibration, e) diameter of the reference, f) type of reference source (back wall, side drilled hole)

g) sound attenuation characteristics of the reflector, h) sound attenuation characteristics of the material under test, i) amplitude correction factor-this is used if the selected reference reflector is a curved back wall as opposed to a flat wall surface type reflector, j) compensation value to compensate for transfer loss differences between the selected reference reflector and the material under test, and k) equivalent reflector size (ERS) value defining a diameter of a disk shaped reflector used for generating DGS curves.

This information is tabulated and the tabulated information is then converted into a digital fomat (digitized). The digitized information can then be conveniently stored within the apparatus for accessing by the processor module. As shown in FIG. 6, when the user calibrates the test apparatus, he inputs into the control module information identifying the type of transducer being used, the reflector being used for calibration, and the type of material being tested. The control module then enables that portion of correlation module 42 in which relevant DGS curve information is stored so as subsequent test data is processed, processor module 36 has can access the information. It will be understood that the apparatus may be microprocessor controlled, and that the DGS curve information is stored in a binary digital format on a microchip, for example, whose contents are accessible through instructions executed by the microprocessor. Regardless, the stored DGS curve information is readily accessible for use in creating the correct display on screen 16.

In displaying a selected ERS curve on display 16, two factors must be considered. These are a) the relative gain must be related to a definable screen height, and b) the logarithmic scale for dB gain must be converted into a linear scale for the display screen. A screen height Hb can be defined as any point on a appropriate ERS curve to be displayed. For example, the maximum value of the ERS curve may be displayed at 80% of the display screen height. Assuming Gsa is a defined point on the curve and Hb is the corresponding screen height, the gain difference dV between the defined point Gsa and the ERSt curve is calculated as:

$dV = Gsa(Sb, ERSt) - Gsa(s, ERSt)$, or $dV = Gsa(Sb, ERSt) - [G(Ld/Nd + S/Nt, ERSt/D) + 2KtS]$.

In this equation,

Sb is the distance sound is propagated into the material,

Ld the delay line length as discussed previously,

Nd near field length of the delay material,

S is the total length of the sound path,

Nt the near field length of the test material,

D the diameter of the transducer, and

Kt the sound attenuation coefficient of the test material.

With respect to linear screen conversion, this can be effected using the equation:

$dV = 20 \log H(s)/Hb$, where,

H(s) is screen height as related to sound path,

Hb is the reference height, and dV is the gain difference as calculated from the previous equation.

As noted previously, DGS gain values are relative only and must referenced based upon the type of test transducer used. The reference point is determined during calibration and will differ based upon whether a backwall or flat plate reflector 15 is used, or a disc reflector 15d, or side drilled hole reflectors (not shown), or circular arc echoes are created by calibration bodies (also not shown). Equations can be derived for each type calibration reflector which may be selected for calibration purposes. In each instance, sensitivity corrections must be made to account for sound attenuation effects. However, once the reference point is established, the method of the invention produces accurate test results, including the generated gate signal, even if the reflections encountered during the test significantly differ from those produced by the reflector with which the transducer and apparatus were calibrated.

What has been described is an ultrasonic flaw detector for testing materials and structures. The flaw detector incorporates a DGS filtering strategy and a method of detector operation in which the DGS automatically compensates processed echo responses for amplitude display purposes; the provision of such a DGS data processing methodology which allows the flaw detector to provide a visual display of flaw test results in which factors such as system gain, range, and delay are automatically taken into account. Use of a flaw detector incorporating the DGS methodology allows the user to quickly and accurately determine whether or not a test specimen passes a flaw detection test. The DGS methodology involves the use of curves for various types of transducers and reflectors used with various system gain settings and these curves are electronically incorporated into the flaw detector. An entire series of DGS curves for different families of transducers and different types of reflectors are incorporated into the instrument. A major advantage of the flaw detector and method of the present invention is that it enables the user to perform an initial calibration using one type of transducer and reflector, but then run tests with a different levels of reflection without having to recalibrate the detector. And, the results of the tests are accurately displayed to the user without him having to refer to DGS curves or display overlays to evaluate the test results. This provides the user much greater flexibility in performing ultrasonic testing than is now possible. The ultrasonic flaw detector incorporating DGS is easy to use and can be used in a wide variety of test situations. Also, the user is now able to use the instrument to perform tests which comply with design specifications requiring testing to verify DGS standards without resort to the number of DGS graphs which he previously had to do.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. A method of performing ultrasonic flaw testing of a material with ultrasonic flaw test apparatus comprising:

generating an electrical pulse having defined pulse characteristics and supplying said electrical pulse to a transducer means said transducer means being selectable from among a plurality of transducer means;

converting the electrical signal to an ultrasonic pulse by the transducer means; propagating the ultrasonic pulse through the material or assembly, the pulse producing echoes when it encounters flaws or discontinuities in the material as it propagates therethrough;

receiving the echoes back at said transducer means;

converting the received echoes by said transducer means back into a reply electrical signal;

processing the reply electrical signal into a visual display signal representing the amplitude of the echoes for a range of propagation times (distances) of the ultrasonic pulse into the material;

visually displaying the processed electrical signal; and, generating a gate signal which is visually displayed with the processed electrical signal, the displayed gate signal corresponding to a maximum amplitude value which represents the maximum flaw size allowable for the test, whereby if the displayed amplitude of the processed electrical signal exceeds the maximum amplitude value the material fails the test, generating the gate signal including emulating a series of DGS curves for the transducer means used during the test to take into account test parameters related to the transducer means and the material so that after an initial calibration is performed using a selected transducer means and a selected reference reflector prior to a test, valid test results are obtained with the transducer means regardless of the distance of the subsequent reflections, generating said gate signal including storing a series of DGS curves for each transducer means which may be selected, the DGS curves providing a gain factor by which the gate signal is uniform throughout for the entire range of propagation times, each series of DGS curves including information relating both to the near range operation of the transducer means and a gain value required to bring the amplitude of a processed reply electrical signal to a predetermined amplitude value, and storing the DGS curves includes creating a DGS table for each type of transducer means used with the apparatus, the table including a series of entries relating to near field distance, amplitude, and the delay velocity associated with the transducer, the type of crystal used in the selected transducer means to convert electrical signals to ultrasonic pulses and vice versa, and the diameter and operating frequency of the crystal whereby the relationship between the displayed amplitude of the processed electrical signal and the gate signal is readily determined so the user can readily ascertain if a flaw test is passed or failed by the material.

2. The method of claim 1 further including selecting a particular transducer means by the person performing the test with the person entering into the apparatus information identifying the particular transducer means selected, and selecting from among the stored DGS curves those relating to the selected transducer means.

3. The method of claim 2 wherein storing the DGS curves for a transducer means includes digitizing the contents of the table and storing the resulting digital values in the apparatus.

4. The method of claim 3 wherein the method further includes incorporating in the table the type of reference reflector used in a calibration, and the diameter of a reference echo which is produced when the selected transducer means is used with a selected reference reflector.

5. The method of claim 4 wherein the method further includes incorporating in the table sound attenuation values for the selected reference reflector and the material under test, amplitude correction values for the selected reference reflector, and transfer loss values relating to the difference in coupling conditions between the selected reference reflector and the material under test.

6. The method of claim 5 wherein the method further includes incorporating in the table an equivalent reflector size which defines the shape of a disk shaped reflector for a DGS curve.

7. In a method of performing ultrasonic flaw testing of a material with ultrasonic flaw test apparatus in which an electrical pulse having defined pulse characteristics is generated and supplied to a transducer means, converted to an ultrasonic pulse which is propagated through the material to produce echoes when is encounters flaws or discontinuities in the material, the echoes being received back at said transducer means and converted into a reply electrical signal which is processed to produce a visual display signal representing the amplitude of the echoes for a range of propagation times (distances) of the ultrasonic pulse into the material, the processed electrical signal being visually displayed, the improvement comprising:

generating a gate signal which is visually displayed with the processed electrical signal, the displayed gate signal corresponding to a maximum amplitude value which represents the maximum flaw size allowable for the test, whereby if the displayed amplitude of the processed electrical signal exceeds the maximum amplitude value the material fails the test, generating the gate signal including storing a series of DGS curves for the transducer means used during the test to take into account test parameters related to the transducer means and the material, defining each DGS curve as a function of the sound propagation qualities of the material under test, the diameter and operating frequency of a crystal used in the transducer means, the type of selected reflector used for the calibration and the diameter of the reflected echo produced by the selected transducer means, the sound attenuation of the selected reference reflector and the material under test, an amplitude correction value which is used if the selected reference reflector is arcuate as opposed to a flat wall surface type of reflector, a compensation value to compensate for transfer loss differences between the selected reference reflector and the material under test, and an equivalent reflector size value defining a diameter of a disk shaped reflector used for generating DGS curves so that after an initial calibration is performed using a selected transducer means and a selected reference reflector prior to a test, valid test results are obtained with the transducer means regardless of the size of the reflections produced during a test.

8. The method of claim 7 wherein generating the DGS curves includes creating a DGS table for each type of transducer means, and storing the tables.

9. The method of claim 8 wherein storing the DGS curves for a transducer means includes digitizing the contents of the table and storing the resulting digital values.

10. Apparatus for performing ultrasonic flaw testing of a material comprising:

means for generating an electrical pulse having defined pulse characteristics;

a transducer probe for conveying the electrical signal to an ultrasonic pulse which propagates through the material, receives an echo whose characteristics are a function of flaws or discontinuities in the material, and for converting the received echo into an electrical reply signal, said probe being selectable from among a plurality of probes;

processing means for processing the electrical reply signal into a visual display signal representing the amplitude of the echo for a range of propagation times (distances) into the material;

means for visually displaying the processed electrical signal; and, correlation means for generating a gate signal which is visually displayed with the processed electrical signal, the displayed gate signal corresponding to a maximum amplitude value which represents the maximum flaw size allowable for the test, whereby if the displayed amplitude of the processed electrical signal exceeds the maximum amplitude value the material fails the test, the correlation means including means for emulating a series of DGS curves for the probe used during the test to take into account test parameters related to the probe and the material so that after an initial calibration of the apparatus is performed using a selected probe and a reference reflector, valid test results are obtained with the probe means regardless of the size of the reflector used in the test, said correlation means including means for storing a digitized table of parameters from which DGS curves are formed, said parameters included in the table including the sound propagation qualities of the material under test, the diameter and operating frequency of a crystal used in the transducer means, the type of selected reflector used for the calibration and the diameter of the reflected echo produced by the selected transducer, the sound attenuation of the selected reference reflector and the material under test, an amplitude correction value which is used if the selected reference reflector is arcuate as opposed to a flat wall surface type of reflector, a compensation value to compensate for transfer loss differences between the selected reference reflector and the material under test, and an equivalent reflector size value defining a diameter of a disk shaped reflector used for generating DGS curves.

11. The apparatus of claim 10 further including interface means by which the user of the apparatus can program the correlation means as to which probe and reflector and used during calibration.

* * * * *

UNITED STATES PATENT AND TRADEMARK OFFICE
CERTIFICATE OF CORRECTION

PATENT NO. : 5,511,425
DATED : April 30, 1996
INVENTOR(S) : Wolf-Dietrich Kleinert et al.

It is certified that error appears in the above-indentified patent and that said Letters Patent is hereby corrected as shown below:

Column 11,

Claim 10, line 5, "convening" should be -- converting --.

Signed and Sealed this

Tenth Day of December, 1996

Attest:

BRUCE LEHMAN

*Attesting Officer*  *Commissioner of Patents and Trademarks*